(12) United States Patent
Gardner et al.

(10) Patent No.: US 7,645,569 B2
(45) Date of Patent: *Jan. 12, 2010

(54) NMR DETECTION OF FOREIGN PAS DOMAIN LIGANDS

(75) Inventors: Kevin H. Gardner, Dallas, TX (US);
Carlos A. Amezcua, Dallas, TX (US);
Paulus J. A. Erbel, Dallas, TX (US);
Paul B. Card, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 744 days.

This patent is subject to a terminal disclaimer.

(21) Appl. No.: 10/677,733

(22) Filed: Oct. 1, 2003

(65) Prior Publication Data

US 2004/0121409 A1 Jun. 24, 2004

Related U.S. Application Data

(60) Continuation-in-part of application No. 10/059,962, filed on Nov. 19, 2001, which is a division of application No. 09/770,170, filed on Jan. 26, 2001, now Pat. No. 6,319,679.

(51) Int. Cl.
*C12Q 1/00* (2006.01)
*G01N 33/53* (2006.01)

(52) U.S. Cl. ............................................. 435/4; 435/7.1

(58) Field of Classification Search ....................... None
See application file for complete search history.

(56) References Cited

U.S. PATENT DOCUMENTS

| 5,843,683 | A | * | 12/1998 | Edery et al. | .................. | 435/7.8 |
| 6,291,429 | B1 | * | 9/2001 | Takahaski et al. | ............. | 514/12 |
| 6,319,679 | B1 | * | 11/2001 | McKnight et al. | ............. | 435/15 |
| 6,436,654 | B1 | * | 8/2002 | Berkenstam et al. | ......... | 435/7.8 |

FOREIGN PATENT DOCUMENTS

WO WO 97/18471 * 5/1997

OTHER PUBLICATIONS

Taylor et al. PNAS, 1999, 63(2):479-506.*

* cited by examiner

*Primary Examiner*—Suzanne M. Noakes
(74) *Attorney, Agent, or Firm*—Richard Aron Osman (57) ABSTRACT

Specific binding of a foreign core ligand to a PAS domain, wherein the PAS domain is predetermined, prefolded in its native state, and comprises a hydrophobic core that has no NMR-apparent a priori formed ligand cavity, is determined using NMR spectra of the PAS domain in the presence and absence of a foreign ligand bound within the hydrophobic core. A functional surface binding specificity of a PAS domain is changed by (a) introducing into the hydrophobic core of the PAS domain a foreign ligand of the PAS domain; and (b) detecting a change in the functional surface binding specificity of the PAS domain.

3 Claims, 4 Drawing Sheets

NMR DETECTION OF FOREIGN PAS DOMAIN LIGANDS

This application is a continuation-in-part of U.S. Ser. No. 10/059,962, filed Nov. 19, 2001, which is a divisional of U.S. Ser. No. 09/770,170, filed Jan. 26, 2001, now U.S. Pat. No. 6,319,679

This work was supported by National Institute of Health Grants CA90601 and CA95471. The U.S. government may have rights in any patent issuing on this application.

INTRODUCTION

1. Field of the Invention

The field of this invention is foreign ligands of PAS protein regulatory domains.

2. Background of the Invention

PAS (Per-ARNT-Sim) domains are protein interaction domains widely used for intra- and intermolecular associations. Database searches indicate that the PAS domain family contains over 3000 members distributed in all kingdoms of life. Structural studies reveal a common mixed a/b fold predicted to be present in all members of this family (Crews & Fan, 1999; Pellequer et al., 1998).

Some members of the PAS family are known to contain small molecules within their cores, allowing them to sense stimuli and regulate diverse biological processes. For example, heme binding by the PAS domains of FixL (Gong et al., 1998; Miyatake et al., 2000) and Dos (Delgado-Nixon et al., 2000) allows bacteria to sense oxygen levels; blue light photoreception in plant phototropins is achieved through a flavin molecule associated with their LOV domains (a PAS domain subclass) (Crosson et al., 2003); and binding of exogenous organic compounds by the C-terminal PAS domain of the aryl hydrocarbon receptor (AhR) displaces a chaperone protein, induces a conformational change and activates the transcription of xenobiotic metabolizing enzymes (Schmidt & Bradfield, 1996). In all these examples, the cofactor is reportedly required for proper folding and functioning of the PAS domain within the context of the holo-protein.

However, for most PAS domains there is no evidence for such a cofactor. In fact, structurally characterized PAS domains without bound cofactors (Amezcua et al., 2002; Erbel et al., 2003; Morais Cabral et al., 1998) show tightly packed cores with no pre-formed cavities that would suggest a cofactor or ligand binding site. In the case of one such PAS domain (PAS kinase) we previously reported screened chemical library compounds could induce chemical shift changes in residues that clustered in hydrophobic core regions analogous to the heme-binding site of FixL (McKnight et al., U.S. Pat. No. 6,319,679). Here we confirm that finding with additional compounds, and with alternative cofactor-free PAS domains.

We also disclose the more remarkable and surprising finding that the introduction of foreign ligands into the hydrophobic core of such PAS domain proteins can induce structural changes distal to the core and change the functional surface binding specificity of the PAS domain. This finding provides a hitherto unknown mechanism for regulating the interaction of PAS domains with their biomolecular targets.

The Robert A. Welch Foundation, Houston, Tex., supported research related to the present invention through grant number I-1424.

Relevant Literature

Some aspects of this disclosure were described in Amezucua et al., October 2002, Structure 10, 1349-1361; in Harper et al., September 2003, Science 301, 1541-4; and in McKnight et al. U.S. Pat. No. 6,319,679.

SUMMARY OF THE INVENTION

The invention provides methods and compositions for detecting foreign PAS domain ligands and for using such ligands to regulate the function of proteins comprising PAS domains.

In one embodiment, the invention provides methods of detecting binding of a PAS domain with a foreign core ligand of the PAS domain, wherein the PAS domain is predetermined, prefolded in its native state, and comprises a hydrophobic core that has no NMR-apparent a priori formed ligand cavity, the method comprising the steps of (a) detecting a first NMR spectrum of the PAS domain in the presence of a foreign ligand; and (b) comparing the first NMR spectrum with a second NMR spectrum of the PAS domain in the absence of the ligand to infer the presence of the ligand specifically bound within the hydrophobic core of the PAS domain. In a preferred embodiment, the recited PAS domain is PAS kinase PAS A.

In another embodiment, the invention provides methods of changing a functional surface binding specificity of a PAS domain, wherein the PAS domain is predetermined, prefolded in its native state, and comprises a hydrophobic core that has no NMR-apparent a priori formed ligand cavity, the method comprising the steps of (a) introducing into the hydrophobic core of the PAS domain a foreign ligand of the PAS domain; and (b) detecting a resultant change in the functional surface binding specificity of the PAS domain.

The recited binding specificity may be a change in intermolecular or intramolecular binding affinity of the PAS domain, and may be manifested in a variety of functional changes, such as a change in kinase activity or specificity, a change in channel patency or specificity, etc.

The PAS domain may be isolated or expressed by and within a host cell or animal, wherein the ligand is foreign to the host, and the change is conveniently detected indirectly or inferentially as a change in host cell or animal physiology precorrelated with the change in binding specificity.

A wide variety of suitable PAS domains may be targeted, including PAS kinase PAS A, NPAS2 PAS A, HIF2a PAS B, HIF1a PASB, ARNT PAS B and human ether-a-go-go related gene (HERG) N-terminal PAS, which are typically present as part of their full-length natural proteins.

DETAILED DESCRIPTION OF PARTICULAR EMBODIMENTS OF THE INVENTION

In one aspect of the invention, we show that foreign ligands can be introduced into the hydrophobic core regions of PAS domains even (a) where the PAS domain does not require a core-bound ligand for formation or function; (b) the PAS domain is fully folded in its native state; c) where there is no NMR-apparent a priori formed core cavity to accommodate such a ligand; and/or (d) wherein the PAS domain is unassociated with any predetermined ligand-dependent heterologous chaperone protein. In contrast, AHR PAS-B binds both HSP90, a common chaperone of unfolded proteins, and ligand, and AHR PAS-B domain is unfolded without ligand (e.g. Kikuchi, et al., 2003, J Biochem 134, 83-90).

This aspect of the invention provides methods and corresponding compositions, kits, instructions and business methods for detecting binding of a PAS domain with a foreign (i.e. not a natural ligand of the PAS domain) core ligand of the PAS domain, wherein the PAS domain is predetermined, prefolded in its native state, and comprises a hydrophobic core that has no NMR-apparent a priori formed ligand cavity, the method comprising the steps of (a) detecting a first NMR spectrum of the PAS domain in the presence of a foreign ligand; and (b) comparing the first NMR spectrum with a second NMR spectrum of the PAS domain in the absence of the ligand to infer the presence of the ligand specifically bound within the hydrophobic core of the PAS domain. In a preferred embodiment, the recited PAS domain is PAS kinase PAS A.

In another aspect of the invention, we show that the introduction of foreign ligands into the hydrophobic core of such PAS domain proteins can induce structural changes distal to the core and change the functional surface binding specificity of the PAS domain. While introducing such a ligand was expected to induce a conformational change within the sequestered core to accommodate the ligand, it was entirely unexpected that such a core ligand introduction would act as a switch to regulate a functional surface binding specificity of the PAS domain. This finding provides a hitherto unknown mechanism for regulating the interaction of PAS domains with their various biomolecular targets.

This aspect of the invention provides methods and corresponding compositions, kits, instructions and business methods for changing a functional surface binding specificity of a PAS domain, wherein the PAS domain is predetermined, prefolded in its native state, and comprises a hydrophobic core that has no NMR-apparent and/or no x-ray crystallographic-apparent a priori formed ligand cavity, the method comprising the steps of (a) introducing into the hydrophobic core of the PAS domain a ligand of the PAS domain such that the ligand stably and specifically binds within the core; and (b) detecting a resultant change in the functional surface binding specificity of the PAS domain.

The recited binding specificity may be a change in intermolecular or intramolecular binding affinity of the PAS domain, such as an inter- or intramolecular PAS-PAS interaction, and may be manifested in a variety of functional changes, such as a change in kinase activity or specificity, a change in channel patency or specificity, etc. Targetable PAS domains are well-known to mediate and regulate a wide variety of functions, and we have found diverse, generalizable examples to be subject to the disclosed ligand regulation.

The PAS domain is typically part of a larger native protein comprising the PAS domain, and may be isolated or expressed by and within a host cell or animal, wherein the ligand is foreign to the host, and the change is conveniently detected indirectly or inferentially as a change in host cell or animal physiology precorrelated with the change in binding specificity. Targetable PAS domains are well-known to mediate and regulate a wide variety of functions which manifest themselves in a corresponding diversity of physiological readouts, and we have found diverse, generalizable examples to be subject to the disclosed ligand regulation. For example, point mutations in a potassium channel subject to PAS domain regulation are known to mediate certain heritable forms of heart disease, which mutations may be rescued by foreign ligand. Hence, the recited change in functional surface binding specificity may result in an inhibition, an enhancement or a restoration of activity or function, depending on the particular application.

Accordingly, a wide variety of suitable PAS domains may be targeted, including PAS kinase PAS A, NPAS2 PAS A, HIF2a PAS B, HIF1a PASB, ARNT PAS B and HERG terminal PAS, which are typically present as part of their full-length natural proteins.

As exemplified below, suitable foreign ligands may be recovered or derived from a wide variety of source materials. Candidate ligands encompass numerous chemical classes, though typically they are organic compounds; preferably small organic compounds and are obtained from a wide variety of sources including libraries of synthetic or natural compounds. Conventional SAR analyses provide ligands of higher affinity and/or specificity. In exemplary embodiments, the foreign ligands are derived from or are structurally similar to those shown below (e.g. Tables 1, 2 and 3).

Pharmaceutical Compositions.

When targeting PAS domains expressed by and within a host cell or animal, the ligands are employed as pharmaceuticals, and the foreign PAS core ligands of this invention are typically administered in the form of a pharmaceutical composition comprising at least one active ligand and a carrier, vehicle or excipient suitable for use in pharmaceutical compositions. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition. Such carriers are well known in the pharmaceutical art as are procedures for preparing pharmaceutical compositions.

Depending on the intended route of delivery, the compositions may be administered in one or more dosage form(s) including, without limitation, liquid, solution, suspension, emulsion, tablet, multi-layer tablet, bi-layer tablet, capsule, gelatin capsule, caplet, lozenge, chewable lozenge, bead, powder, granules, dispersible granules, cachets, douche, suppository, cream, topical, inhalant, aerosol inhalant, patch, particle inhalant, implant, depot implant, ingestible, injectable, or infusion.

The dosage forms may include a variety of other ingredients, including binders, solvents, bulking agents, plasticizers etc. Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches and derivatives, as well as other conventional binders well known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide. The plasticizers used in the dissolution modifying system are preferably previously dissolved in an organic solvent and added in solution form. Preferred plasticizers may be selected from the group consisting of diethyl phthalate, diethyl sebacate, triethyl citrate, crotonic acid, propylene glycol, butyl phthalate, dibutyl sebacate, castor oil and mixtures thereof, without limitation. As is evident, the plasticizers may be hydrophobic as well as hydrophilic in nature. Water-insoluble hydrophobic substances, such as diethyl phthalate, diethyl sebacate and castor oil are used to delay the release of water-soluble drugs, such as potassium chloride. In contrast, hydrophilic plasticizers are used when water-insoluble drugs are employed which aid in dissolving the encapsulating film, making channels in the surface, which aid in drug release.

A wide variety of orally administerable compositions may be used. In a particular embodiment, the oral compositions are provided in solid discrete, self-contained dosage units, such as tablets, caplets, lozenges, capsules, gums, etc., which may comprise or be filled with liquid or solid dosage of the ligand. A wide variety of dosages may be used, depending on the application and empirical determination; typical dosages range from 10 ug to 1 g, preferably at least 100 ug, more preferably at least 1 mg, more preferably at least 10 mg, most preferably at least 100 mg.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the ligand is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the ligand in such compositions is typically a minor component, often being from about 0.05 to 10% by weight with the remainder being the injectable carrier and the like.

The above described components for orally administrable or injectable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The dosage forms of the present invention involve the administration of an active therapeutic substance or multiple active therapeutic substances in a single dose during a 24 hour period of time or multiple doses during a 24 hour period of time. The doses may be uneven in that each dose is different from at least one other dose.

The subject compositions may be administered to effect various forms of release, which include, without limitation, immediate release, extended release, controlled release, timed release, sustained release, delayed release, long acting, pulsatile delivery, etc., using well known procedures and techniques available to the ordinary skilled artisan. A description of representative sustained release materials can be found in the incorporated materials in Remington's Pharmaceutical Sciences.

The following formulation examples illustrate representative pharmaceutical compositions of this invention. The present invention, however, is not limited to the following exemplified pharmaceutical compositions.

Formulations

Formulation 1—Tablets: A compound (e.g. HIF-2a PAS B lead ligand, Table 3) is admixed as a dry powder with a dry gelatin binder in an approximate 1:2 weight ratio. A minor amount of magnesium stearate is added as a lubricant. The mixture is formed into 240-270 mg tablets (80-90 mg of active HIF-2a PAS B ligand per tablet) in a tablet press.

Formulation 2—Capsules: A compound (e.g. HIF-2a PAS B lead ligand, Table 3) is admixed as a dry powder with a starch diluent in an approximate 1:1 weight ratio. The mixture is filled into 250 mg capsules (125 mg of active HIF-2a PAS B ligand compound per capsule).

Formulation 3—Liquid: A compound (e.g. HIF-2a PAS B lead ligand, Table 3) (50 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets: The compound (e.g. HIF-2a PAS B lead ligand, Table 3) is admixed as a dry powder with a dry gelatin binder in an approximate 1:2 weight ratio. A minor amount of magnesium stearate is added as a lubricant. The mixture is formed into 450-900 mg tablets (150-300 mg of active HIF-2a PAS B ligand compound) in a tablet press.

Formulation 5—Injection: The compound (e.g. HIF-2a PAS B lead ligand, Table 3) is dissolved in a buffered sterile saline injectable aqueous medium to a concentration of approximately 5 mg/ml.

Formulation 6—Ointment: The compound (e.g. HIF-2a PAS B lead ligand, Table 3) (2 g) is blended with isopropyl myristate 81 g, fluid paraffin oil 9 g and silica (Aerosil 200, 9 g, Degussa AG, Frankfurt).

Formulation 7—Ointment: The compound (e.g. HIF-2a PAS B lead ligand, Table 3) (23 g) is blended with pharmaceutical-grade white 100 g petroleum jelly.

Formulation 8—Non-ionic water-in-oil cream: The compound (e.g. HIF-2a PAS B lead ligand, Table 3) (100 g) is blended with a mixture of emulsified lanolin 39 g alcohols, of waxes and of oils (Anhydrous eucerin, BDF), methyl para-hydroxybenzoate 0.075 g, propyl para-hydroxybenzoate 0.075 g and sterile demineralized 100 g water.

Formulation 9—Lotion: The compound (e.g. HIF-2a PAS B lead ligand, Table 3) (2 g) is blended with polyethylene glycol (PEG 400) 69 g and 95% Ethanol 30 g.

Formulation 10—Hydrophobic ointment: The compound (e.g. HIF-2a PAS B lead ligand, Table 3) (2 g) is blended with isopropyl myristate 36 g, silicone oil (Rhodorsil 36.400 g 47 V 300, Rhone-Poulenc), beeswax 13 g and silicone oil (Abil 300 100 g cst, Goldschmidt).

Formulation 11—Non-ionic oil-in-water cream: The compound (e.g. HIF-2a PAS B lead ligand, Table 3) (2 g) is blended with cetyl alcohol 4 g, glyceryl monostearate 2.5 g, PEG 50 stearate 2.5 g, Karite butter 9.2 g, propylene glycol 2.0 g, methyl para-hydroxybenzoate 0.075 g, propyl para-hydroxybenzoate 0.075 g and sterile demineralized 100 g water.

Applications

Because targetable PAS domains play myriad and critical roles in cell regulation and interactions, as therapeutics and/or prophylactics, the ligands of this invention are useful for treating a wide variety of medical dysfunctions and diseases, in humans and other animals. For example, targeting mediators of hypoxia-induced pathologies provides therapy for medical conditions such as stroke and cardiac infarction.

Targetable disorders are generally divided into disorders of the central and peripheral nervous system and disorders of the peripheral organs. Targetable disorders of the CNS include stroke, aging, neurodegenerative conditions, such as Alzheimer's disease, Parkinsonism, concussion, aneurysm, ventricular hemorrhage and associated vasospasm, migraine and other vascular headaches, spinal cord trauma, neuroanesthesia adjunct, HIV-dementia and the like. Disorders of the peripheral nervous system include diabetic peripheral neuropathy and traumatic nerve damage. Peripheral organ disease includes atherosclerosis (both diabetic and spontaneous), chronic obstructive pulmonary disease (COPD), pancreatitis, pulmonary fibrosis due to chemotherapeutic agents, angioplasty, trauma, burns, ischemic bowel disease, wounds, ulcers and bed sores, lupus, ulcerative colitis, organ transplantation, renal hypertertsion, overexertion of skeletal muscle, epistaxis (pulmonary bleeding), autoimmune conditions, such as systemic lupus (erythematosus), multiple sclerosis and the like; and inflammatory conditions, such as inflammatory bowel disease, rheumatoid arthritis, septic shock, erythema nodosum leprosy, septicemia, uveitis, etc.

Accordingly, in one of its method aspects, this invention provides a method for treating a patient with a targetable disease or condition, said method comprising administering to said patient a pharmaceutical composition comprising a pharmaceutically acceptable carrier and an effective disorder-treating subject ligand. In a preferred embodiment of this method, the disorder treated is stroke.

Administration

The subject compositions may be formulated for administration by any route, including without limitation, oral, buccal, sublingual, rectal, parenteral, topical, inhalational, including itnranasal, injectable, including subcutaneous, intravenous, intramuscular, etc., topical, including transdermal, etc. The subject compositions are administered in a pharmaceutically (including therapeutically, prophylactically and diagnostically) effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

Intravenous dose levels for treating acute medical conditions range from about 0.1 mg/kg/hour to at least 10 mg/kg/hour over a period of from about 1 to about 120 hours and especially 24 to 96 hours. Preferably, an amount of at least about 0.2 mg/kg/hour is administered to the patient. A preloading bolus of from about 10 mg to about 500 mg may also be administered to achieve adequate steady state levels. While intravenous administration is preferred for acute treatments, other forms of parenteral administration, such as intramuscular injection can be used as well. In such cases, dose levels similar to those described above may be employed.

Another acute condition which can be advantageously treated with the ligands of this invention is acute oxidative damage to the cardiovascular system, such as the damage which occurs in a patient who has suffered a cardiac infarction or the like. When treating such a condition, a pharmaceutical composition comprising a subject ligand is administered parenterally, e.g. intravenously, at doses similar to those described above for stroke and other acute CNS conditions.

As discussed above, the compounds described herein are suitable for use in a variety of drug delivery systems. Injection dose levels for treating neurodegenerative, autoimmune and inflammatory conditions range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.02 to about 50 mg/kg of ligand, with preferred doses each providing from about 0.04 to about 30 mg/kg and especially about 1 to about 10 mg/kg.

When used to prevent the onset of a degenerative condition, such as a neurodegenerative, autoimmune or inflammatory condition, the ligands of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition. When used prophylactically, a pharmaceutical composition comprising a subject ligand is administered orally to the predisposed patient. The doses for this oral therapy will typically be the same as those set forth above for treating persons suffering from the neurodegenerative, autoimmune or inflammatory condition.

The compounds of this invention can be administered as the sole active agent or they can be administered in combination with other agents, including other active subject ligand.

In yet further aspects, the invention provides a method of modulating a binding activity of an immunophilin FK-506 binding protein (FKBP), the method comprising the steps of: (a) contacting the FKBP with a ligand selected from the group consisting of 2-phenylimidazole, KG-190, KG-720, KG-373 and KG-510; and (b) detecting a modulation of the binding activity of the FKBP.

In yet further aspects, the invention provides a method of modulating a binding activity of a Rho GDP-dissociation inhibitor (GDI), the method comprising the steps of: (a) contacting the GDI with a ligand selected from the group consisting of KG-406, KG-654 and KG-509; and (b) detecting a modulation of the binding activity of the GDI.

Examples Identifying and Functionally Validating Foreign Ligands

An initial set of 550 compounds was purchased from commercial sources based on the following criteria: a) the molecular frameworks and sidechains of selected compounds were similar to those previously established by computational methods to preferentially bind proteins (Fejzo, 1999; Hajduk et al., 2000a), b) the chemicals contained at least one hydrogen bond donor/acceptor atom (to increase water solubility) and an average MW of 203±73 Da, and c) the compounds were available in >0.5 g quantities at an average price of US $40/g. An additional 223 compounds were acquired that either helped to fill underrepresented chemical classes or showed structural similarities to initial PASK PAS A and HIF-2a PAS B hits.

To demonstrate the chemical diversity of our library we performed a two-dimensional similarity analysis using Tanimoto coefficients (Willet et al., 1986) obtained from the 2048 bit Daylight Fingerprints (Daylight Chemical Systems). The Tanimoto coefficients provide a measure of similarity between pairs of molecules represented by a set of pre-defined chemical descriptors. Typical values for the Tanimoto coefficients range between 0 and 1.0, where identical compounds are given a value of 1.0. This analysis was used to generate a self-organizing map (SOM) (Kohonen, 2001) that converted our complex high-dimensional similarity data into a two-dimensional grid of clusters, where a given cluster represents an array of compounds with high similarity. The SOM for our library contained 120 clusters with an average cluster size of 7 compounds. The compounds were then mapped on a previously generated SOM for the NCI open database of 251,250 compounds providing a qualitative measure of diversity, and confirming that this library is a large collection of chemicals from organic synthesis and natural source extracts that cover a wide chemical space (Voigt et al., 2001).

The chemical library was screened using $^1H/^{15}N$-HSQC NMR experiments in order to obtain direct information about binding sites and determine ligand specificity. Mixtures of five compounds and protein were analyzed initially. The samples with largest chemical shift changes were then deconvoluted by recording additional HSQC experiments on the individual components of the mixture, thus revealing the compound or compounds responsible for the observed effects. Once the hits were identified, equilibrium dissociation constants were obtained after titrating increasing amounts of compound to protein in a series of $^1H/^{15}N$-HSQC experiments or by titrating protein to a dilute ligand solution using isothermal titration calorimetry (ITC). For the following analysis, only compounds with $K_d<1$ mM were considered hits.

Figure 1:
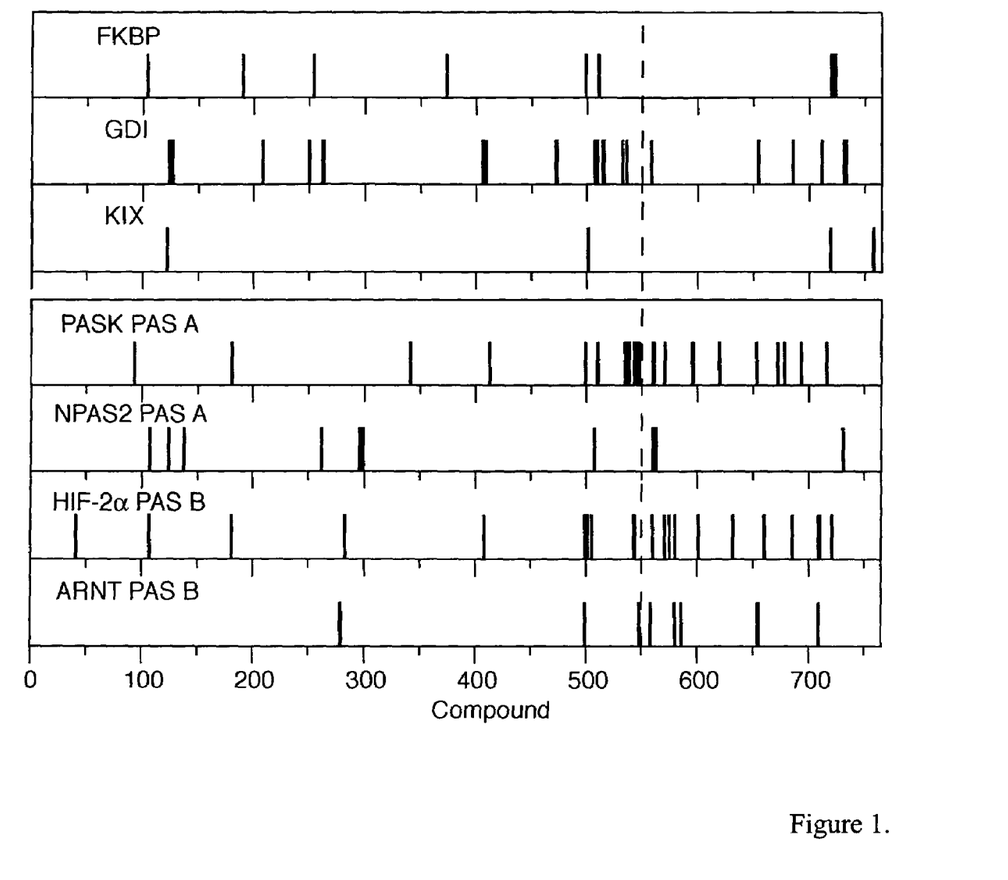
FIG. 1. Correlation of NMR-derived hits for several screened proteins where each bar represents a compound with $K_d \leq 1$ mM.

As shown below, the library was screened against three proteins with known ligand-binding or protein-binding regions (FKBP, GDI, and KIX) and four PAS domains without identified binding sites (PASK PAS A, HIF-2a PAS B, ARNT PAS B, and NPAS2 PAS A). Out of the 760 compounds, 70 were hits for at least one protein, 16 showed binding for two, one showed affinity for three, and only one compound associated with four proteins (FIG. 1). Based on equilibrium dissociation constants, target selectivity, and chemical shift effects we identified specific hits for every protein. Compound affinities varied between $10^{-3}$ and $10^{-6}$ M producing hit ratios of 0.5-3.0%. The hit ratios observed for hPASK PAS A and HIF-2a PAS B (3.0% and 2.8% respectively) are slightly higher than the other two PAS domains as a result of the addition of several compounds to the library based on initial hits from the screen of the first 550 chemicals.

Validation of the Screening Library for Ligand-Binding Site Discovery

To validate our chemical library as a discovery tool, we conducted two control NMR-screens against proteins known to bind ligands and previously studied by NMR. The first control target was the immunophilin FK-506 binding protein (Michnick et al., 1991; Rosen et al., 1991). Over the past few years, this protein has been the target of NMR-based screens from which several ligands have been identified and the ligand-binding region has been characterized (Hajduk et al., 1997; Shuker et al., 1996).

Figure 2:
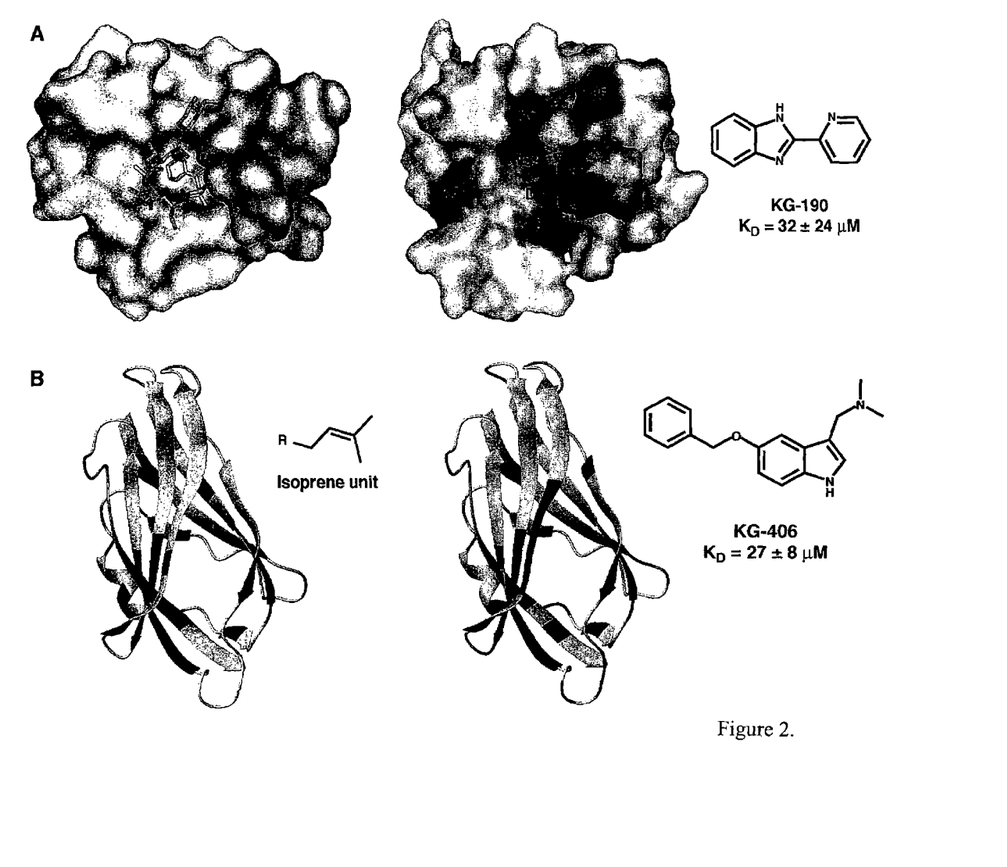
FIG. 2. A) Surface representation of FKBP comparing the binding location for FK-506 (left) and KG-190 (right). B) Ribbon diagram of the N-terminal domain of GDI comparing the residues affected (shaded) upon addition of isoprenylated Cdc42 peptides (left) and KG-406 (right).

A total of 8 hits with binding affinities better than 1 mM were found during our $^1H/^{15}N$-HSQC-based NMR screen (FIG. 1). The map of residues with chemical shift changes (Dd)>0.075 ppm, FIG. 2A (right), shows that compound KG-190 interacts with FKBP in the same region where FK-506 (shown shaded on the left) is bound in the crystal structure of the FKBP/FK-506 complex (Van Duyne et al., 1991). Using one-dimensional NMR methods it has previously been shown (Hajduk et al., 1997) that a compound related to KG-190, 2-phenylimidazole, selectively binds FKBP. Other hits from this screen interacted with the protein in a similar fashion but with lower affinities (scheme IA), demonstrating the ability of our library to identify a relevant binding site.

Scheme I. A) Selected hits from the FKBP screen showing their chemical structures and measured equilibrium dissociation constants. The compound 2-Phenylimidazole is shown for reference (see text). B) Representative compounds found to bind GDI (left) and compounds related to KG-406 for which no binding was detected (right).

Our second control was the C-terminal domain of the Rho GDP-dissociation inhibitor (GDI). This protein interacts with the carboxy-terminal isoprene unit of the Rho family members through the residues highlighted in red at the C-terminal hydrophobic cavity (Gosser et al., 1997) shown in FIG. 2B (left). Out of sixteen identified hits (FIG. 1), compound KG-406 was the tightest binder showing an affinity of 27 mM for this protein. The set of amide groups whose chemical shifts are significantly affected (Dd>0.092 ppm) by binding of this compound to GDI (FIG. 2B, right) are localized around the same hydrophobic cavity involved in isoprene binding. Interestingly, the related compound 5-benzyloxyindole (KG-407) which lacks the sidechain substitution at position 3 and other indole derivatives (KG-158 and KG-727) missing the benzyloxy moiety do not bind GDI (scheme IB), thereby demonstrating the binding specificity of KG-406.

The two control screening experiments showed that the compounds in our library are well-suited for the rapid identification of ligands and their binding sites. In addition, the GDI example shows that our chemical collection can provide structural activity relationship (SAR) data, which may be used for the synthesis or purchase of compounds with higher affinities.

PAS Kinase

The first PAS domain protein for which a ligand binding site discovery was made using this library is the PAS A domain of PAS Kinase. The kinase domain of this protein, involved in regulation of sugar metabolism and translation (Rutter et al., 2001a), is partially inhibited by direct interaction with its N-terminal PAS domain. We have recently reported that a series of diphenylmethanes, found during a NMR screen (Amezcua et al., 2002), selectively bind at the same site where heme and flavin mononucleotide (FMN) are localized in the crystal structures of FixL (Gong et al., 1998; Miyatake et al., 2000) and Phy3 (Crosson & Moffat, 2001) respectively. The later two proteins are also PAS-containing kinases regulated by their PAS domains. This discovery, together with our mutational and biochemical studies, inform the mode of kinase regulation by the PAS domain.

To resolve the structural motifs required for ligand binding affinity and specificity, we synthesized several analogs of the diphenylmethanes found in our screen (Amezcua et al., 2002). Examination of Tables 1 and 2 indicates that substitutions affecting the phenyl rings or the bulk size at the central carbon dramatically alter ligand affinity. For example, we observed that para substitutions have higher affinities for PASK PAS A (compound 2 vs 3 and 4 vs 7 in Table 1), while bicyclic functional groups like in compound 10 abolish binding to the protein. In addition, table 2 shows that larger substituents ($R_1$) also increase the compound's affinity. $^1H/^{15}N$-HSQC experiments of individual compounds with $^{15}N$-labeled PASK PAS A indicate that all of the ligands bind to the same site, indicating that the diphenylmethane framework is specific for this protein and that further chemical derivatization may be performed to produce a higher affinity ligand.

Our structural studies confirm that core ligand binding induces changes in the structure and/or dynamics of the Fα helix, Hβ strand, and adjacent kinase binding FG loop that disrupt inhibitory PAS/kinase interactions (e.g. Amezcua et al., Struture 2002, supra), and functional binding and kinase assays confirm resultant changes in kinase activity and substrate binding specificity.

NPAS2

Neuronal PAS protein 2 (NPAS2) is a PAS-containing basic helix-loop-helix (bHLH) transcription factor that binds DNA together with its obligate dimeric partner BMAL1, another PAS-bHLH transcription factor. NPAS2 is primarily expressed in the mammalian forebrain where it plays a role in long-term memory acquisition and in regulation of the cicardian rhythm (Garcia et al., 2000; Reick et al., 2001). Recent studies have shown that DNA/NPAS2/BMAL1 complex formation is doubly regulated by the redox state of the nicotinamide adenine dinucleotide (NAD) cofactor (Rutter et al., 2001b) and via CO binding to heme groups attached to both PAS domains of NPAS2 (Dioum et al., 2002). We have not observed the presence of heme in NPAS2 PAS A when expressed from bacterial cultures (E. coli) grown in minimal media despite the fact that this ligand has previously been found from a longer fragment of the protein (Dioum et al., 2002).

Figure 3:
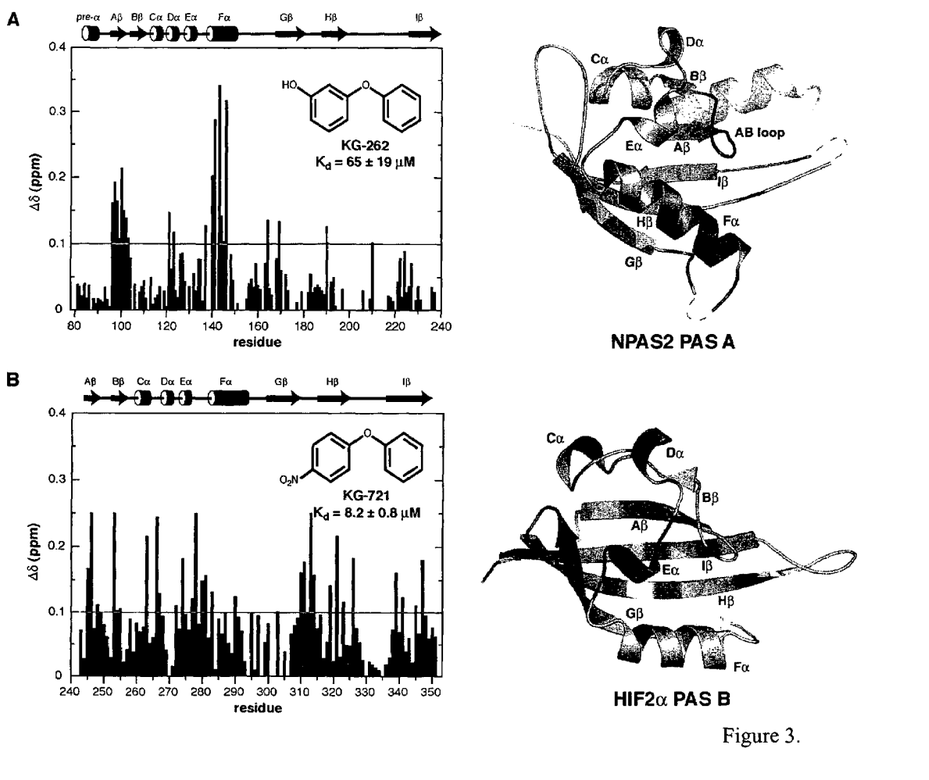
FIG. 3. A) Chemical shift changes plotted against residue number (left) and map of shifting residues with Dd>0.1 ppm (top 20%) on the ribbon diagram of the theoretical model of NPAS2 PAS A (right) for [protein]=0.25 mM and [ligand]= 0.5 mM. The secondary structure elements are shown on top of the bar chart for reference. B) Minimum chemical shift changes observed when 0.4 mM of HIF-2a PAS B were mixed with 0.5 mM of compound KG-721.

A three dimensional homology-model of NPAS2 PAS A was calculated using the X-Ray structure of FixL (Miyatake et al., 2000) as a template in order to identify the ligand binding site for the hits of this screen. Several experimentally determined constraints including hydrogen bonds, NOEs, and secondary structure elements (see methods section below) from a previous structural study (Holdeman & Gardner, 2001) were used in the calculation. As shown in FIG. 1, a total of 10 hits with equilibrium dissociation constants tighter than 1 mM were identified. Analysis of the hits indicated that NPAS2 PAS A favors biphenyl ethers and N-benzylanilines for binding. The bar chart of FIG. 3A displays the measured chemical shift changes of the $^1H/^{15}N$-HSQC peaks for a 0.25 mM protein solution with and without 0.5 mM of compound KG-262 ($K_d$=65±19 mM by NMR). As indicated by the red colored residues on the theoretical model of NPAS2 PAS A, the area most affected is between the AB loop and the Fa helix. This region was also used for binding by the other nine hits from the screen. Interestingly, it is the Fa helix which provides the axial histidine of the pentacoordinated heme iron in FixL (Miyatake et al., 2000) indicating that all our hits have successfully identified the putative heme-binding region in NPAS2 PAS A.

Our structural confirm that core ligand binding induces distal changes in NPAS2 PAS A structure, and functional binding confirm resultant changes in NPAS2:ARNT1 complex formation and DNA binding specificity (e.g. Rutter et al., 2001, Science 293, 510-514).

HIF and ARNT

The hypoxia inducible factor (HIF) is a protein complex that mediates responses to lowered oxygen levels in mammalian cells (Semenza, 1999). This is a heterodimeric complex composed of two bHLH-PAS containing proteins (Wang et al., 1995) HIFa and ARNT (Aryl Hydrocarbon Nuclear Translocator). The C-terminal PAS domains (PAS B) of both proteins interact with each other conferring increased stability to the DNA:HIFa:ARNT transcriptional initiation complex. The high resolution structure of HIF2a PAS B (Erbel et al., 2003) shows a well folded domain lacking the dynamic regions of hPASK PAS A and long insertion loops of NPAS2 PAS A. In the case of ARNT PAS B, only a theoretical model based on the structure of photoactive yellow protein (PYP) has been published (Pellequer et al., 1999). Structural work from our group indicates that this protein is also well folded and free of unusually flexible regions. Since the protein/protein interaction mechanism between HIF-2a PAS B and ARNT PAS B is of particular interest in our laboratory, we screened these two proteins against our library to look for binding regions.

Figure 4:
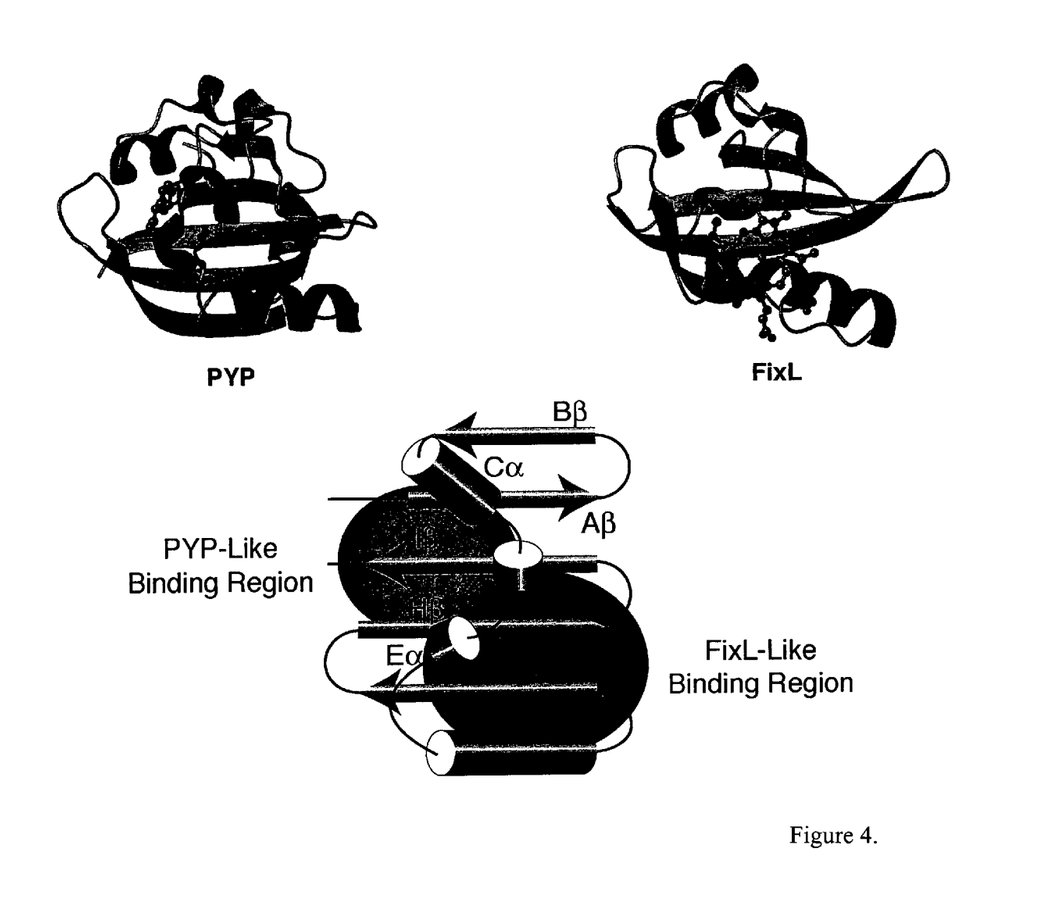
FIG. 4. Schematic representation of a typical PAS domain indicating the two distinct ligand-binding areas: PYP-like (shaded, top sphere) and FixL-like (darker shaded, bottom sphere). The ribbon diagrams for the PYP and FixL showing their bound cofactors are displayed for reference.

As seen in FIG. 1, 21 hits were obtained for HIF-2a PAS B and 9 for ARNT PAS B. Three compounds were hits for both proteins: KG-499, KG-580, and KG-709. The first one was also a hit for hPASK PAS A and FKBP, suggesting it is a non-specific binder, while the last two showed different affinities for each protein (15 mM and 230 mM for HIF-2a, and 840 mM and 647 mM for ARNT respectively). An example of the typical chemical shift effects caused by the tightest binding compounds of the HIF-2a PAS B screen can be observed in the bar graph of residue number versus Dd in FIG. 3B. Compound KG-721, as well as X others, showed slow exchange behavior in the NMR experiments, i.e., peaks disappearing and reappearing at some other location in the spectra, therefore making it hard to track them without fully reassigning them. An estimated Dd value was obtained by the minimum chemical shift method (Farmer et al., 1996), which calculates the distance between each peak on the reference spectra and their closest one on the experiment with added ligand. This method generally provides a very similar account of the most affected residues when compared to an absolute determination of Dd. The ribbon diagram of affected residues (FIG. 3B) shows that HIF-2a PAS B uses a different interface than PASK PAS A and NPAS2 PAS B for ligand binding. In fact, this area, formed by helices Ca, Da, and Ea as well as adjacent segments of the beta sheet resembles the ligand-binding pocket of PYP. Interestingly, most structurally characterized PAS domains, e.g., FixL, Phy3, and PASK interact with ligands through the Fa helix and the adjacent Gb and Hb strands (FIG. 4). HIF-2a PAS B is therefore the first mammalian PAS domain shown to use a PYP-like region for protein/ligand interactions.

Our structural studies confirm that core ligand binding in each HIF-2a PAS B and ARNT PAS B induces distal changes in PAS domain structure, and functional binding studies confirm resultant changes in DNA:HIF-2a:ARNT transcription complex formation and DNA binding specificity (e.g. Michel et al., Biochim Biophys Acta. 2002 Oct. 11; 1578(1-3):73-83). Table 3 show exemplary identified foreign ligands of HIF-2a PAS B and ANRT PAS B, respectively, which specifically bind within their hydrophobic cores and disrupt complex formation.

We have observed two distinct ligand-binding regions within the generic PAS fold. The first one is a FixL-like cavity involving the inner residues of the beta sheet and the Fa helix while the second one is a PYP-like region formed between helices Ca, Da, and Ea and strands Ab, Hb, and Ib. The observed binding region in PASK PAS A, and NPAS2 PAS A, belonged to the first class, while HIF-2a PAS B was of the later type. FIG. 4 shows the structures of PYP, FixL, and Phy3 with their bound cofactors and a schematic representation of the PAS fold highlighting the two different ligand-binding sites. These two ligand-binding regions give the PAS fold not only the ability to accommodate distinct ligand classes, but also a greater versatility for signal transduction.

We have successfully used NMR-based ligand screening as a tool for the discovery of ligand-binding sites. This method can be easily applied to members of any protein family in order to study their protein/ligand properties, provided they are amenable for NMR spectroscopy. Other methods for the discovery of ligand-binding sites have used organic solvents as probes (Buhrman et al., 2003; Byerly et al., 2002) and although these methods have proven useful, the chemical space covered by organic solvents is limited. Our methods promptly identify ligand-binding sites by taking advantage of the more specific interactions and larger chemical diversity from the compounds in our library.

Materials and Methods

Library Design. The screening library was assembled by purchasing 762 commercially available organic compounds. Stock solutions at a concentration of 50 mM were prepared by dissolution of the compounds in $d_6$-DMSO. When necessary, ethanolamine or acetic acid were titrated to the stock solutions until the addition of 1 mM of each compound stock resulted in no change in the pH of a 50 mM phosphate buffer. The working set of compound stocks was kept at 4° C. while the master stocks were stored at −80° C. in order to minimize any possible degradation from repeated freeze/thaw cycles.

Protein Expression and Purification. All U-$^{15}$N-labeled recombinant proteins were expressed in transformed *E. coli* (BL-21 DE3) cultures, induced with 0.5 mM IPTG, grown overnight at 20° C. using minimal M9 media with $^{15}$N-ammonium chloride as the sole nitrogen source. Human PASK PAS A (Amezcua et al., 2002), murine NPAS2 PAS A (Holdeman & Gardner, 2001), human HIF2a PAS B, and human ARNT PAS B (Erbel et al., 2003) were obtained as previously described. Human FKBP(1-108) was cloned and expressed as a His$_6$-Gbl fusion protein using a modified version of the pHIS.Parallel1 vector (Sheffield et al., 1999). Nickel affinity chromatography was used to purify both the fusion protein and FKBP after cutting with TEV protease. The final buffer for NMR experiments contained 25 mM sodium acetate at pH=5.0. Bovine Rho-GDI(60-204) was purified by a two step cation exchange chromatography using linear salt gradients over Source 15S and Mono-S columns (Amersham Biosciences). The buffer was finally exchanged to 20 mM sodium phosphate, 1 mM EDTA, 2 mM DTT, pH=6.0.

NMR Experiments. All NMR experiments were recorded on a Varian Unity Inova spectrometer operating at a proton frequency of 500 MHz, equipped with a SMS autosampler (Varian, Inc.), and a 50-position sample tray. The data was processed with NMRPipe (Delaglio et al., 1995) and analyzed with NMRView (Johnson, 1994). A typical 2D $^{15}$N/$^1$H-HSQC experiment was recorded on samples containing 0.22-0.25 mM of U-$^{15}$N-labeled protein in the appropriate buffer containing 10% $D_2O$. For the primary screen, each protein sample was mixed with 5 compounds at a final concentration of 0.5 mM each. Similar studies have used higher compound concentrations and larger number of compounds per sample, e.g. 1 mM and up to 100 compounds (Hajduk et al., 1999; Hajduk, 1997), however, 0.5 mM/compound and 5 compounds/mixture were a good compromise between the number of observed hits and the amount of protein used for the following steps. Identification of hits was easily accomplished through an in-house module written for NMRView that uses the minimum chemical shift method (Farmer et al., 1996) to rank spectra $(Dd=[dH^2+(dN*0.1)^2]^{1/2})$. Deconvolution of hits was done by adding the individual components of the mix (0.5 mM) to a protein sample (0.25 mM) and ranking the spectra in a similar fashion as described above.

Determination of Binding Constants. Equilibrium dissociation binding constants were determined by $^{15}$N/$^1$H-HSQC titration experiments for ligands interacting with the protein on a fast exchange time scale. A typical titration series consisted of 0.25 mM protein and increasing ligand concentrations of 0.05, 0.1, 0.2, 0.35, 0.5, 0.75, and 1 mM. Average dissociation constants were obtained by analyzing the data with a titration analysis routine written for NMRView that uses an interface to XMGRACE to fit moving peaks as described previously (Amezcua et al., 2002).

Isothermal titration calorimetry was used to confirm NMR-estimated binding constants for compounds showing intermediate or slow exchange behavior. Typically, a concentrated solution of protein (1-1.2 mM) was titrated to a diluted ligand solution (0.05 mM) to ensure ligand solubility (the protein was also titrated to buffer alone for reference substraction) and the data was analyzed with the software provided by the manufacturer (MicroCal, Inc.).

Homology Model of NPAS2 PAS A. A sequence alignment was initially generated between the PAS domain of the FixL protein from *Rhizobium meliloti* (residues: 131-251) and the PAS A domain of murine NPAS2 (residues: 78-240) using VectorNTI (InforMax, Inc.). Initial results gave poor alignments at the C-terminal end due to the presence of a 20-residue insertion loop in mNPAS2. A satisfactory sequence alignment was generated when residues 211-221 were eliminated from the alignment algorithm and then put back into the sequence. The program Modeller v.6 (Sali & Blundell, 1993) was then used to generate a homology model of NPAS2 using the X-Ray structure of rmFixL (PDB code: 1D06) and the generated alignment. In addition, several NMR-generated constraints were included into the model: a) TALOS-predicted (Cornilescu et al., 1999) secondary structure elements (residues in strands: 97-102, 106-111, 160-174, 184-199, and 223-235; residues in helices: 82-92, 112-117, 120-124, 127-132, and 140-150), b) 26 hydrogen bond constraints, c) 90 short-range HN-HN NOEs (i-i+1,i-i+2, and i-i+3), and d) 33 long-range HN-HN NOEs |i-j|.

REFERENCES

Amezcua, C. A., Harper, S. M., Rutter, J. & Gardner, K. H. (2002). Structure and interactions of PAS kinase N-terminal PAS domain: model for intramolecular kinase regulation. *Structure (Camb)* 10(10), 1349-61.

Borgstahl, G. E. O., Williams, D. R. & Getzoff, E. D. (1995). 1.4 A Structure of Photoactive Yellow Protein, a Cytosolic Photoreceptor: Unusual Fold, Active Site, and Chromophore. *Biochemistry* 34, 6278-6287.

Buhrman, G., de Serrano, V. & Mattos, C. (2003). Organic Solvents Order the Dynamic Swith II in Ras Crystals. *Structure (Camb)* 11, 747-751.

Byerly, D. W., Mcelroy, C. A. & Foster, M. P. (2002). Mapping the surface of *Escherichia coli* peptide deformylase by NMR with organic solvents. *Protein Science* 11, 1850-1853.

Cornilescu, G., Delaglio, F. & Bax, A. (1999). Protein backbone angle restraints from searching a database for chemical shift and sequence homology. *Journal of Biomolecular NMR* 13(3), 289-302.

Crews, S. T. & Fan, C. M. (1999). Remembrance of things PAS: regulation of development by bHLH-PAS proteins. *Curr Opin Genet Dev* 9(5), 580-7.

Crosson, S. & Moffat, K. (2001). Structure of a Flavin-binding plant photoreceptor domain: Insights into light-mediated signal transduction. *Proceedings of the National Academy of Sciences of the United States of America* 98(6), 2995-3000.

Crosson, S., Rajagopal, S. & Moffat, K. (2003). The LOV domain family: photoresponsive signaling modules coupled to diverse output domains. *Biochemistry* 42(1), 2-10.

Dalvit, C., Flocco, M., Knapp, S., Mostardini, M., Perego, R., Stockman, B. J., Veronesi, M. & Varasi, M. (2002). High-throughput NMR-based screening with competition binding experiments. *J Am Chem Soc* 124(26), 7702-9.

Delaglio, F., Grzesiek, S., Vuister, G. W., Zhu, G., Pfeifer, J. & Bax, A. (1995). NMRPipe: a multidimensional spectral processing system based on UNIX pipes. *J Biomol NMR* 6(3), 277-93.

Delgado-Nixon, V. M., Gonzalez, G. & Gilles-Gonzalez, M. A. (2000). Dos, a heme-binding PAS protein from *Escherichia coli*, is a direct oxygen sensor. *Biochemistry* 39(10), 2685-91.

Denison, M. S. & Nagy, S. R. (2003). Activation of the aryl hydrocarbon receptor by structurally diverse exogenous and endogenous chemicals. *Annu Rev Pharmacol Toxicol* 43, 309-34.

Dioum, E. M., Rutter, J., Tuckerman, J. R., Gonzalez, G., Gilles-Gonzalez, M. A. & McKnight, S. L. (2002). NPAS2: a gas-responsive transcription factor. *Science* 298(5602), 2385-7.

Erbel, P. J. A., Card, P. B., Karakuzu, O., Bruick, R. K. & Gardner, K. H. (2003). Structural basis for PAS domain heterodimerization in the bHLH-PAS transcription factor HIF. *Proc Natl Acad Sci USA*.

Farmer, B. T., 2nd, Constantine, K. L., Goldfarb, V., Friedrichs, M. S., Wittekind, M., Yanchunas, J., Jr., Robertson, J. G. & Mueller, L. (1996). Localizing the NADP+ binding site on the MurB enzyme by NMR. *Nat Struct Biol* 3(12), 995-7.

Fejzo, J., Lepre, C. A., Peng, J. W., Bemis, G. W., Ajay, Murcko, M. A. and Moore, J. M. (1999). The SHAPES strategy: an NMR-based approach for lead generation in drug discovery. *Chemistry & Biology* 6, 755-769.

Garcia, J. A., Zhang, D., Estill, S. J., Michnoff, C., Rutter, J., Reick, M., Scott, K., Diaz-Arrastia, R. & McKnight, S. L. (2000). Impaired cued and contextual memory in NPAS2-deficient mice. *Science* 288(5474), 2226-30.

Gong, W. M., Hao, B., Mansy, S. S., Gonzalez, G., Gilles-Gonzalez, M. A. & Chan, M. K. (1998). Structure of a biological oxygen sensor: A new mechanism of heme-driven signal transduction. *Proceedings of the National Academy of Sciences of the United States of America* 95(26), 15177-15182.

Gosser. Y. Q., Nomanbhoy, T. K., Aghazadeh, B., Manor, D., Combs, C., Cerione, R. A. & Rosen, M. K. (1997). C-terminal binding domain of Rho GDP-dissociation inhibitor directs N-terminal inhibitory peptide to GTPases. *Nature* 387(6635), 814-9.

Gu, Y. Z., Hogenesch, J. B. & Bradfield, C. A. (2000). The PAS superfamily: sensors of environmental and developmental signals. *Annu Rev Pharmacol Toxicol* 40, 519-61.

Hajduk, P. J., Betz, S. F., Mack, J., Ruan, X., Towne, D. L., Lerner, C. G., Beutel, B. A., & Fesik, S. W. (2002). A Strategy for High-Throughput Assay Development Using Leads Derived from Nuclear Magnetic Resonance-Based Screening. *Journal of Biomolecular Screening* 7(5), 429-432.

Hajduk, P. J., Bures, M., Praestgaard, J. & Fesik, S. W. (2000a). Privileged molecules for protein binding identified from NMR-based screening. *J Med Chem* 43(18), 3443-7.

Hajduk, P. J., Gerfin, T., Boehlen, J. M., Haberli, M., Marek, D. & Fesik, S. W. (1999). High-throughput nuclear magnetic resonance-based screening. *J Med Chem* 42(13), 2315-7.

Hajduk, P. J., Gomtsyan, A., Didomenico, S., Cowart, M., Bayburt, E. K., Solomon, L., Severin, J., Smith, R., Walter, K., Holzman, T. F., Stewart, A., McGaraughty, S., Jarvis, M. F., Kowaluk, E. A. & Fesik, S. W. (2000b). Design of adenosine kinase inhibitors from the NMR-based screening of fragments. *J Med Chem* 43(25), 4781-6.

Hajduk, P. J., Olejniczak, E. T. & Fesik, S. W. (1997). One-Dimensional Relaxation- and Diffusion-Edited NMR Methods for Screening Compounds That Bind to Macromolecules. *J. Am. Chem. Soc.* 119, 12257-12261.

Hajduk, P. J., Sheppard, G., Nettesheim, D. G., Olejniczak, E. T., Shuker, S. B., Meadows, R. P., Steinman, D. H., Carrera, G. M., Marcotte, P. A., Jr., Severin, J., Walter, K., Smith, H., Simmer, R., Holzman, T. F., Morgan, D. W., Davidsen, S. K., Summers, J. B., & Fesik, S. W. (1997). Discovery of Potent Nonpeptide Inhibitors of Stromelysin Using SAR by NMR. *J. Am. Chem. Soc.* 119, 5818-5827.

Holdeman. T. C. & Gardner, K. H. (2001). 1H, 13C and 15N chemical shift assignments of the N-terminal PAS domain of mNPAS2. *J Biomol NMR* 21(4), 383-4.

Johnson. B. A. a. B., R. A. (1994). NMRView: A computer program for the visualization and analysis of NMR data. *Journal of Biomolecular NMR* 4, 603-614.

Kohonen. T. (2001). *Self-Organizing Maps*. Third edit. Series in Information Sciences, 20, Springer, Heidelberg.

Michnick. S. W., Rosen, M. K., Wandless, T. J.. Karplus, M. & Schreiber, S. L. (1991). Solution structure of FKBP, a rotamase enzyme and receptor for FK506 and rapamycin. *Science* 252(5007), 836-9.

Miyatake, H., Mukai, M., Park, S. Y., Adachi, S., Tamura, K., Nakamura, H., Nakamura, K., Tsuchiya, T., Iizuka, T. & Shiro, Y. (2000). Sensory mechanism of oxygen sensor FixL from *Rhizobium meliloti*: crystallographic, mutagenesis and resonance Raman spectroscopic studies. *J Mol Biol* 301(2), 415-31.

Morais Cabral, J. H., Lee, A., Cohen, S. L., Chait, B. T., Li, M. & Mackinnon, R. (1998). Crystal structure and functional analysis of the HERG potassium channel N terminus: a eukaryotic PAS domain. *Cell* 95(5), 649-55.

Parsons, L. B., N.; Eisenstein, E.; Gilson, M.; Kairys, V.; Orban, J. (2003). Solution Structure and Functional Ligand Screening of HI0719, a Highly Conserved Protein from Bacteria to Humans in the YjgF/YER057c/UK114 Family. *Biochemistry* 42(1), 80-89.

Pellecchia, M. S., D. S.; Wütrich, K. (2002). NMR IN DRUG DISCOVERY. *Nature Reviews Drug Discovery* 11, 211-219.

Pellequer, J. L., Brudler, R. & Getzoff, E. D. (1999). Biological sensors: More than one way to sense oxygen. *Curr Biol* 9(11), R416-8.

Pellequer, J. L., Wager-Smith, K. A., Kay, S. A. & Getzoff, E. D. (1998). Photoactive yellow protein: a structural prototype for the three-dimensional fold of the PAS domain superfamily. *Proc Natl Acad Sci USA* 95(11), 5884-90.

Reick, M., Garcia, J. A., Dudley, C. & McKnight, S. L. (2001). NPAS2: an analog of clock operative in the mammalian forebrain. *Science* 293(5529), 506-9.

Rosen, M. K., Michnick, S. W., Karplus, M. & Schreiber, S. L. (1991). Proton and nitrogen sequential assignments and secondary structure determination of the human FK506 and rapamycin binding protein. *Biochemistry* 30(19), 4774-89.

Rutter, J., Michnoff, C. H., Harper, S. M., Gardner, K. H. & McKnight, S. L. (2001a). PAS Kinase: An evolutionary conserved PAS domain-regulated serine/threonine kinase. *Proceedings of the National Academy of Sciences of the United States of America* 98, 8991-8996.

Rutter, J., Reick, M., Wu, L. C. & McKnight, S. L. (2001b). Regulation of clock and NPAS2 DNA binding by the redox state of NAD cofactors. *Science* 293(5529), 510-4.

Sali, A. & Blundell, T. L. (1993). Comparative protein modelling by satisfaction of spatial restraints. *J Mol Biol* 234 (3), 779-815.

Schmidt, J. V. & Bradfield, C. A. (1996). Ah receptor signaling pathways. *Annu Rev Cell Dev Biol* 12, 55-89.

Semenza, G. L. (1999). Regulation of mammalian O2 homeostasis by hypoxia-inducible factor 1. *Annu Rev Cell Dev Biol* 15, 551-78.

Sheffield, P., Garrard, S. & Derewenda, Z. (1999). Overcoming expression and purification problems of RhoGDI using a family of "parallel" expression vectors. *Protein Expression and Purification* 15(1), 34-39.

Shuker, S. B., Hajduk, P. J., Meadows, R. P. & Fesik, S. W. (1996). Discovering high-affinity ligands for proteins: SAR by NMR. *Science* 274(5292), 1531-4.

Stephenson, K. & Hoch, J. A. (2001). PAS-A domain of phosphorelay sensor kinase A: a catalytic ATP-binding domain involved in the initiation of development in *Bacillus subtilis. Proc Natl Acad Sci USA* 98(26), 15251-6.

Stockman, B. J. D., C. (2002). NMR screening techniques in drug discovery and drug design. *Progress in Nuclear Magnetic Resonance Spectroscopy* 41, 187-231.

Taylor, B. L. & Zhulin, I. B. (1999). PAS domains: internal sensors of oxygen, redox potential, and light. *Microbiol Mol Biol Rev* 63(2), 479-506.

van Dongen, M. J., Uppenberg, J., Svensson, S., Lundback, T., Akerud, T., Wikstrom, M. & Schultz, J. (2002). Structure-based screening as applied to human FABP4: a highly efficient alternative to HTS for hit generation. *J Am Chem Soc* 124(40), 11874-80.

Van Duyne, G. D., Standaert, R. F., Karplus, P. A., Schreiber, S. L. & Clardy, J. (1991). Atomic structure of FKBP-FK506, an immunophilin-immunosuppressant complex. *Science* 252(5007), 839-42.

Voigt, J. H., Bienfait, B., Wang, S. & Nicklaus, M. C. (2001). Comparison of the NCI Open Database with Seven Large Chemical Structural Databases. *Journal of Chemical Information and Computer Sciences* 41, 702-712.

Waller, C. L. & McKinney, J. D. (1995). Three-dimensional quantitative structure-activity relationships of dioxins and dioxin-like compounds: model validation and Ah receptor characterization. *Chem Res Toxicol* 8(6), 847-58.

Wang, G. L., Jiang, B. H., Rue, E. A. & Semenza, G. L. (1995). Hypoxia-inducible factor 1 is a basic-helix-loop-helix-PAS heterodimer regulated by cellular O2 tension. *Proc Natl Acad Sci USA* 92(12), 5510-4.

Willet, P., Winterman, V. & Badwen. D. (1986). Implementation of nearest neighbour searching in an online chemical structure search system. *Journal of Chemical Information and Computer Sciences* 26, 36-41.

Figure Descriptions

FIG. 1. Correlation of NMR-derived hits for several screened proteins where each bar represents a compound with $K_d \leq 1$ mM. The hit ratios are as follows: PASK PAS A, 3.0%; HIF-2a PAS B, 2.8%; ARNT PAS B, 1.4%, NPAS2 PAS A, 1.3%; KIX, 0.5%; GDI, 2.9%; FKBP, 1.0%. The dashed line indicates a second set of compounds purchased after the first 550 chemicals were screened against PASK PAS A and HIF-2a PAS B. This set includes follow up compounds for the last two proteins as well as additional molecules selected to fill underrepresented chemical classes.

FIG. 2. A) Surface representation of FKBP comparing the binding location for FK-506 (left) and KG-190 (right). The top 20% residues affected by addition of 0.5 mM of KG-190 to 0.25 mM of protein are shaded (Dd>0.075 ppm). PDB accession codes: 1FKF (left) and 1FKT (right). B) Ribbon diagram of the N-terminal domain of GDI comparing the residues affected (shaded) upon addition of isoprenylated Cdc42 peptides (left) and KG-406 (right). As for FKBP, the structure on the right shows the 20% most affected residues (Dd>0.092 ppm) after mixing 0.5 mM of KG-406 with 0.25 mM of protein. The GDI PDB accession code is 1AJW.

FIG. 3. A) Chemical shift changes plotted against residue number (left) and map of shifting residues with Dd>0.1 ppm (top 20%) on the ribbon diagram of the theoretical model of NPAS2 PAS A (right) for [protein]=0.25 mM and [ligand]= 0.5 mM. The secondary structure elements are shown on top of the bar chart for reference. Residues highlighted in darker shading are those located above the horizontal grey line in the chart. The figure also shows the chemical structure of compound KG-262, which has an affinity for the protein of 65±19 mM. B) Minimum chemical shift changes observed when 0.4 mM of HIF-2a PAS B were mixed with 0.5 mM of compound KG-721 ($K_d$=8±0.8 mM as determined by ITC). The residues with Dd>0.1 ppm (top 20%) are shown in red on the ribbon diagram of the lowest energy structure from 1P97 (PDB). The protein pictures were drawn with Pymol.

FIG. 4. Schematic representation of a typical PAS domain indicating the two distinct ligand-binding areas: PYP-like (shaded, top sphere) and FixL-like (darker shaded, bottom sphere). The ribbon diagrams for the PYP and FixL showing their bound cofactors are displayed for reference. PDB accession codes are: 2PHY (PYP) and 1D06 (FixL). The ribbon diagrams were drawn using MolMol.

The foregoing examples are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

A. Selected Hits for FKBP

B. Binding and Non-Binding Compounds from the GDI Screen

TABLE 1

| R | $K_d$ |
|---|---|
| ![1] 4-hydroxy-3-nitrophenyl | 9.4 ± 3.4 μM* |
| ![2] 4-cyanophenyl | 44 ± 20 μM* |
| ![3] 3-cyanophenyl | 91 ± 34 μM |
| ![4] 4-hydroxyphenyl | 97 ± 46 μM |
| ![5] 4-fluorophenyl | 156 ± 57 μM |

TABLE 1-continued

[Structure: 4-(2-hydroxyphenyl)propan-2-yl group with R substituent]

| R | $K_d$ |
|---|---|
| 6  [2-amino-4-methylphenol] | 250 ± 38 μM |
| 7  [3-hydroxy-methylbenzene] | 340 ± 110 μM |
| 8  [4-methylbenzamide, CONH₂] | 503 ± 131 μM |
| 9  [4-methylpyridine] | 1.7 ± 0.5 mM |
| 10 [2-methylbenzofuran] | No binding |

*$K_d$ was measured by ITC.

TABLE 2

[Structure: bis(4-hydroxyphenyl)methane with R₁ and H substituents]

| R₁ | $K_d$ |
|---|---|
| 11 t-Bu | 8.2 ± 2.8 μM* |
| 12 Ph | 12.2 ± 3.2 μM* |
| 13 CCl₃ | 54 ± 30 μM |
| 14 i-Pr | 114 ± 69 μM |

TABLE 2-continued

[Structure: bis(4-hydroxyphenyl)methane with R₁ and H substituents]

| R₁ | $K_d$ |
|---|---|
| 15 Me | 300 ± 95 μM |
| 16 H | 357 ± 176 μM |

*$K_d$ was measured by ITC.

TABLE 3

[Structure: N-benzyl-4-(trifluoromethyl)-2-nitroaniline]

Lead compound: Kd = 0.8-1 μM (by ITC; by NMR: slow exchange)
Disrupt complex formation: Yes HIF-2a PAS B ligand

[Structure: 5-(3,5-bis(trifluoromethyl)phenyl)-1H-tetrazole]

Lead compound; slow exchange; Kd = 150-250 μM
Disrupts complex formation: Yes

ARNT PAS B ligand

What is claimed is:

1. A method of detecting binding of a PAS (Per-ARNT-Sim) domain of a protein with a foreign core ligand of the PAS domain, wherein the PAS domain is prefolded in its native state, the method comprising the steps of:
   determining from NMR analysis of the PAS domain that the PAS domain comprises a hydrophobic core that has no NMR-apparent a priori formed ligand cavity;
   detecting a first NMR spectrum of the PAS domain in the presence of the foreign ligand;
   comparing the first NMR spectrum with a second NMR spectrum of the PAS domain in the absence of the ligand; and therefrom
   determining the presence of the ligand specifically bound within the hydrophobic core of the PAS domain.

2. The method of claim 1, wherein the PAS domain is the PAS A domain of PAS kinase.

3. The method of claim 1 wherein the protein consists of the PAS domain.

* * * * *